Feb. 24, 1942. E. M. FEHR Plant Pat. 503

APRICOT

Filed July 31, 1940

INVENTOR.
Emma Marie Fehr

BY J. Ralph Fisher
ATTORNEY.

Patented Feb. 24, 1942

Plant Pat. 503

UNITED STATES PATENT OFFICE

503

APRICOT

Emma Marie Fehr, Lewiston, Idaho

Application July 31, 1940, Serial No. 348,676

1 Claim. (Cl. 47—62)

The present invention relates to a distinct and new variety of apricot tree which I discovered growing in my flower garden at Lewiston Orchards, Idaho.

Its value as a superior variety was recognized as a young tree and it was transplanted to my orchard where it now stands. It is probably a natural cross of the Moorpark and the Yakimine since these two varieties were growing in the immediate vicinity at the time of its origin, and it resembles, in some way, each of these two varieties.

From a commercial standpoint, the new variety is especially valuable because of its unusual productivity and the large size of its fruit. In addition, the fruit ripens early, is very firm, keeps well, cans well, is juicy, and has a flavor of extra fine quality.

Figure 1:
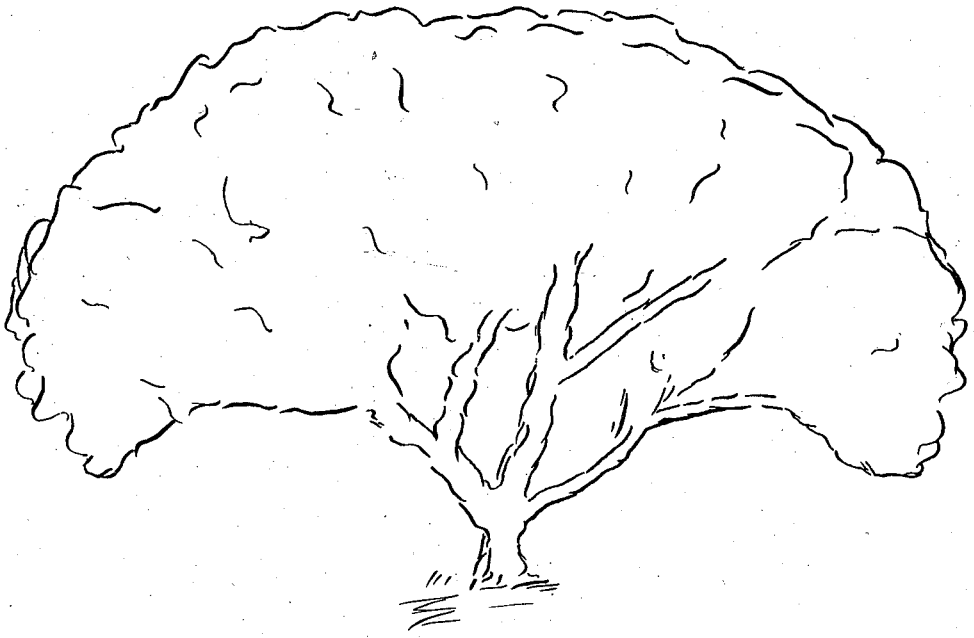
Figure 3:
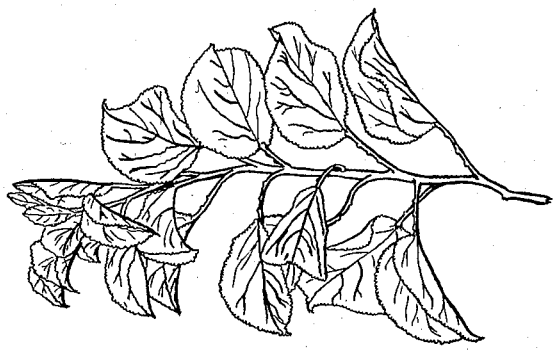
Figure 2:
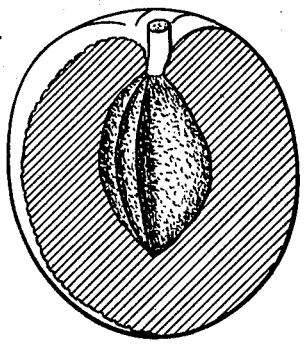

Having generally described the new variety which has been asexually reproduced, I will now more particularly set forth the prominent distinctions and characteristics thereof. Referring to the accompanying drawing, Figure 1 illustrates the general form of my new variety of apricot tree, Figure 2 is a longitudinal section of the fruit, and Figure 3 is a sprig of the tree.

As illustrated, my new tree is a large, spreading, open, round-topped tree with a stocky trunk of medium smoothness. It has wide, heavy crotches and stocky branches with a glossy medium smooth dark brown bark well covered with gray scarf skin. The twigs are of a deep maroon color partially covered with gray scarf skin and a few large gray lenticels. The foliage is very abundant, resembling the Yakimine in many ways. The tree is a strong vigorous grower comparatively free from disease of any kind and makes a very attractive tree.

The leaves are medium large being from two and one-quarter to three and three-quarter inches long and from two and one-quarter to three and one-half inches wide in the fully grown tree, smooth, ovate shaped, acutely pointed, medium thick with finely crenate margins, dark glossy green on the upper surface and lighter green on the lower surface, free from fuzz or plant-hairs and thus remaining clean from dust which is common in my irrigated orchard. The petioles are of medium length, that is, one and one-half to two inches long, of medium thickness, strong and with linear stipules, of a maroon red color and they have from two to five large green globose alternate glands distributed in some cases along the full length of the petiole and in some cases positioned near the leaf blade.

The tree is a regular and an exceptionally heavy producer. It is hardy and relatively immune to spring frosts, requires regular orchard thinning and ripens its fruit evenly a week to ten days ahead of the Moorpark. For example, the tree illustrated, which is growing in Lewiston Orchards, Idaho, and which has a spread of 37 feet and a height of 12 to 14 feet, produced in the spring of 1940 a yield of 897 pounds of marketable fruit, and the fruit ripened in June and was all ready to pick and market June 30.

The fruit buds are free and non-pubescent, short, plump, of medium size, hardy, abundant and well distributed over the twigs and spurs. The flowers are of medium size and are white with a pink tinge. Blooming takes place early or about a week ahead of the Moorpark. In the example above referred to, the tree bloomed about March 15.

The fruit is uniformly large, being two to two and one-half inches long and from two to two and one-fourth inches in diameter. It is of an even, oval oblong form, has a narrow, abrupt deep wavy cavity, a short heavy stem, and a small depressed apex. Opposite sutures divide the fruit into equal halves. One suture is rather deep and abrupt near the stem, becoming a line toward the apex, and is distinctly marked by a series of small pits along its entire length, deeper and more pronounced near the cavity. The color of the fruit is a mottled orange yellow when ripe with a light carmine blush on the exposed side.

The skin of the fruit is free, thin, firm, tough, fine-grained and sparsely covered with a fine silky fuzz and an occasional deep carmine dot. The flesh is melting firm, of a deep orange color, of fine texture, medium-juicy and buttery when ripe and has a rich, mild or aromatic, sub-acid flavor of extra fine quality. The pits are free, corrugated of a slightly oval form, blunt pointed, large size, and are conspicuously winged with three prominent and two minor ribs extending the full length of the pit.

The fruit ripens slowly after harvest, from the pit out, handles well and remains in good condition from six to ten days in ordinary storage. It will usually keep from four to six days longer than the Moorpark. The firmness of the flesh during the ripening period with no soft quarters gives this variety a superior shipping quality as compared to the Moorpark. The fruit cans well, holds its color and has a very rich, mild, pleasant flavor.

What I claim is:

A new and distinct variety of apricot tree, characterized particularly by its vigorous growth, early ripening and heavy production of fruit of superior size, rich mild sub-acid flavor of fine quality, firm flesh and superior handling and canning qualities, substantially as shown and described.

EMMA MARIE FEHR.